United States Patent [19]

Epp et al.

[11] Patent Number: 5,068,189

[45] Date of Patent: Nov. 26, 1991

[54] RECOMBINANT DNA VECTORS ENCODING A 4"-O-ISOVALERYL ACYLASE DERIVED FROM A CARBOMYCIN BIOSYNTHETIC GENE, DESIGNATED CARE, FOR USE IN STREPTOMYCES AND OTHER ORGANISMS

[75] Inventors: Janet K. Epp, Indianapolis; Brigitte E. Schoner, Monrovia, both of Ind.

[73] Assignee: Eli Lilly and Company, Indianapolis, Ind.

[21] Appl. No.: 194,672

[22] Filed: May 13, 1988

[51] Int. Cl.$^5$ .................... C12N 15/52; C12N 15/76; C12N 9/00
[52] U.S. Cl. .................... 435/183; 435/69.1; 435/71.1; 435/72; 435/91; 435/119; 435/169; 435/172.1; 435/172.3; 435/252.3; 435/252.35; 435/320.1; 435/886; 536/7.1; 536/27; 935/9; 935/14; 935/22; 935/29; 935/38; 935/59; 935/60; 935/61; 935/66; 935/76

[58] Field of Search .................... 435/69.1, 71.1, 72, 435/91, 119, 169, 172.1, 172.3, 183, 252.35, 252.3, 320, 886; 536/27, 7.1; 935/9, 14, 22, 29, 38, 59, 60, 61, 66, 76

[56] References Cited

U.S. PATENT DOCUMENTS 4,935,340  6/1990  Baltz et al. .................... 435/6

OTHER PUBLICATIONS

Epp et al., 1987, Gene, 53:73.

*Primary Examiner*—Richard A. Schwartz
*Assistant Examiner*—Richard C. Peet
*Attorney, Agent, or Firm*—Douglas K. Norman; Leroy Whitaker

[57] ABSTRACT

The carE gene of *Streptomyces thermotolerans* has been isolated and used to construct recombinant DNA expression vectors. The carE gene encodes 4"-O-isovaleryl acylase activity important in the biosynthesis of a number of useful antibiotics. The carE gene can be used not only to construct recombinant cells with an increased ability to produce the acylase enzyme but also to construct recombinant cells with the ability to produce novel antibiotic compounds.

27 Claims, 7 Drawing Sheets

Restriction Site and Function Map of Plasmid pOJ171
(~45 kb)

Restriction Site and Function Map of Plasmid pOJ160
(~7 kb)

Restriction Site and Function Map of Plasmid pOJ313
(~10.8 kb)

Restriction Site and Function Map of Plasmid pOJ159
(10.65 kb)

Restriction Site and Function Map of Plasmid pOJ230
(~9.4 kb)

Restriction Site and Function Map of Plasmid pOJ235.

Restriction Site and Function Map of Plasmid pCZR111
(6395 bp)

RECOMBINANT DNA VECTORS ENCODING A 4"-O-ISOVALERYL ACYLASE DERIVED FROM A CARBOMYCIN BIOSYNTHETIC GENE, DESIGNATED CARE, FOR USE IN STREPTOMYCES AND OTHER ORGANISMS

SUMMARY OF THE INVENTION

The present invention relates to a novel gene, designated carE, that encodes a 4"-O-isovaleryl acylase enzyme, methods for using the carE gene, recombinant DNA cloning vectors that encode the acylase enzyme, transformants containing the vectors, and the enzyme produced by the transformants. *Streptomyces thermotolerans* produces carbomycin, a macrolide antibiotic consisting of a 16-member cyclic lactone and two sugar residues, mycarose and mycaminose. The antibiotic activity of carbomycin, like that of other macrolides, is due to inhibition of protein synthesis by a mechanism that involves the binding of carbomycin to the ribosome. The biosynthesis of carbomycin involves the attachment of an isovaleryl group (derived from isovaleryl coenzyme A) at the 4"-OH position of the mycarose residue mediated by an acylase enzyme. The carE gene encodes a 4"-O-isovaleryl acylase activity.

The present invention provides expression vectors that encode the isovaleryl acylase useful in Streptomyces and many other host cells. The development and exploitation of recombinant DNA technology in Streptomyces has been driven by the desire to improve the antibiotic-producing ability of this industrially important organism, not only to increase antibiotic yield, but also to produce novel antibiotics. This development has been somewhat retarded by the low number of antibiotic biosynthetic genes presently available for use in modifying Streptomyces by recombinant DNA technology. The present invention is useful and especially important in that it expands the number of antibiotic biosynthetic genes suitable for such use.

The vectors of the present invention are particularly useful, because the vectors can be introduced into and selected for in a variety of Streptomyces cells. Streptomyces provides over half of the clinically important antibiotics and thus is a commercially significant group. The present invention provides new and useful vectors and methods not only for this industrially important group but also for other antibiotic-producing organisms and allows for increasing the yield of carbomycin in fermentations and also for producing new antibiotics and antibiotic derivatives.

For purposes of the present invention, as disclosed and claimed herein, the following terms are defined below.

AmR — the apramycin resistance-conferring gene.

Antibiotic — a substance produced by a microorganism which, either naturally or with limited modification, will inhibit the growth of or kill another microorganism or eukaryotic cell.

Antibiotic Biosynthetic Gene — a DNA segment that encodes one or more activities that can mediate the biochemical process of converting primary metabolites into antibiotics.

Antibiotic Biosynthetic Pathway — an entire set of antibiotic biosynthetic genes minimally required for the process of converting primary metabolites into antibiotics.

Antibiotic-Producing Organism — any organism, including, but not limited to, Actinoplanes, Actinomadura, Bacillus, Cephalosporium, Micromonospora, Penicillium, Nocardia, and Streptomyces, which either produces an antibiotic or contains genes which, if expressed, would produce an antibiotic.

Antibiotic Resistance-Conferring Gene — a DNA segment that encodes an enzymatic or other activity that confers resistance to an antibiotic.

ApR — the ampicillin resistance-conferring gene.

Bifunctional Cloning Shuttle Vector — a recombinant DNA cloning vector that can replicate and/or integrate into organisms of two different taxa.

carA — a carbomycin resistance-conferring gene of type A.

carB — a carbomycin resistance-conferring gene of type B.

carG — a DNA sequence that comprises one or more genes that encode the activities required to form the 16-member cyclic lactone of carbomycin.

carE — a DNA sequence that can be isolated from *Streptomyces thermotolerans* that encodes a 4"-O-isovaleryl acylase activity.

Cloning — the process of incorporating a segment of DNA into a recombinant DNA cloning vector and transforming a host cell with the recombinant DNA.

cos — the lambda cohesive end sequence.

Cosmid — a recombinant DNA cloning vector which not only can replicate in a host cell in the same manner as a plasmid but also can be packaged into phage heads.

Gene — a DNA sequence that comprises a promoter and coding sequence positioned so that the promoter drives transcription of the coding sequence.

Genetic Library — a set of recombinant DNA cloning vectors into which segments of DNA, comprising substantially all of the DNA of a particular organism, have been cloned.

Hybridization — the process of annealing two single-stranded DNA molecules to form a double-stranded DNA molecule, which may or may not be completely basepaired.

NmR — the neomycin resistance-conferring gene.

ori — a plasmid origin of replication.

Phasmid—a recombinant DNA vector that may act as a phage or as a plasmid.

Recombinant DNA Cloning Vector — any autonomously replicating or integrating agent, including, but not limited to, plasmids, comprising a DNA molecule to which one or more additional DNA molecules can be or have been added.

Restriction Fragment — any linear DNA molecule generated by the action of one or more restriction enzymes.

rRNA — ribosomal ribonucleic acid.

Sensitive Host Cell — a host cell that cannot grow in the presence of a given antibiotic without a DNA segment that confers resistance thereto.

TcR — the tetracycline-resistant phenotype or gene conferring same.

Transductant — a recipient host cell that has undergone transformation by recombinant phage infection.

Transformant — a recipient host cell that has undergone transformation.

Transformation — the introduction of DNA into a recipient host cell that changes the genotype and results in a change in the recipient cell.

tsrR — the thiostrepton-resistant phenotype or gene conferring same.

BRIEF DESCRIPTION OF THE FIGURES

The figures described below are drawn to scale; however, observed restriction fragment size may vary somewhat from calculated size based on map distances. For some restriction enzymes, such as MboI, only certain cut sites are shown for convenience.

DETAILED DESCRIPTION OF THE INVENTION

The present invention relates to a novel gene, designated carE, that encodes a 4"-O-isovaleryl acylase activity. Recombinant DNA expression vectors that encode the acylase can be used to increase antibiotic yield and to produce new antibiotics. The coding sequence of the carE gene is useful in a method for increasing the 4"-O-isovaleryl acylase activity in an organism. The method comprises transforming the organism with a recombinant DNA vector that codes for expression of the carE gene product and culturing the transformed cell under conditions suitable for gene expression.

Figure 1:
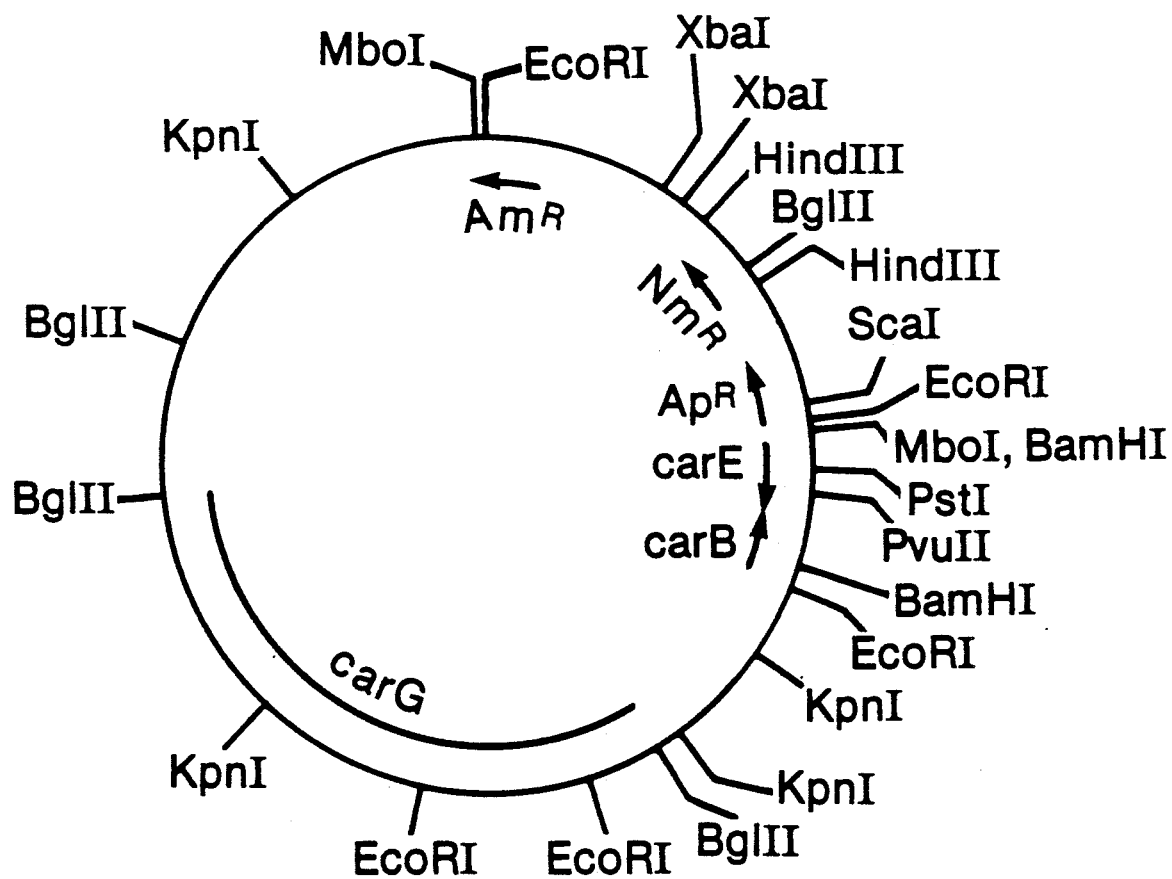
FIG. 1 is a restriction site and function map of plasmid pOJ171.

The carE gene was isolated from a carbomycin-producing strain of *Streptomyces thermotolerans*, available from the American Type Culture Collection, Rockville, Md. 20852 under the accession number ATCC 11416. Thus, genomic DNA of *S. thermotolerans* was partially digested with restriction enzyme MboI, and the resulting DNA was inserted into HpaI-BamHI-digested cosmid pKC462A (available from the Agricultural Research Service, Northern Regional Research Center, Peoria, Ill. 61604, under the accession number NRRL B-15973) to yield a number of carE-containing plasmids, including plasmid pOJ171. Plasmid pOJ171 (FIG. 1) can be isolated from *E. coli* K12 SF8/pOJ171 (NRRL B-18169) as described in Example 1. The carE gene can be isolated from plasmid pOJ171 on an ~3.8 kb EcoRI restriction fragment.

Figure 4:
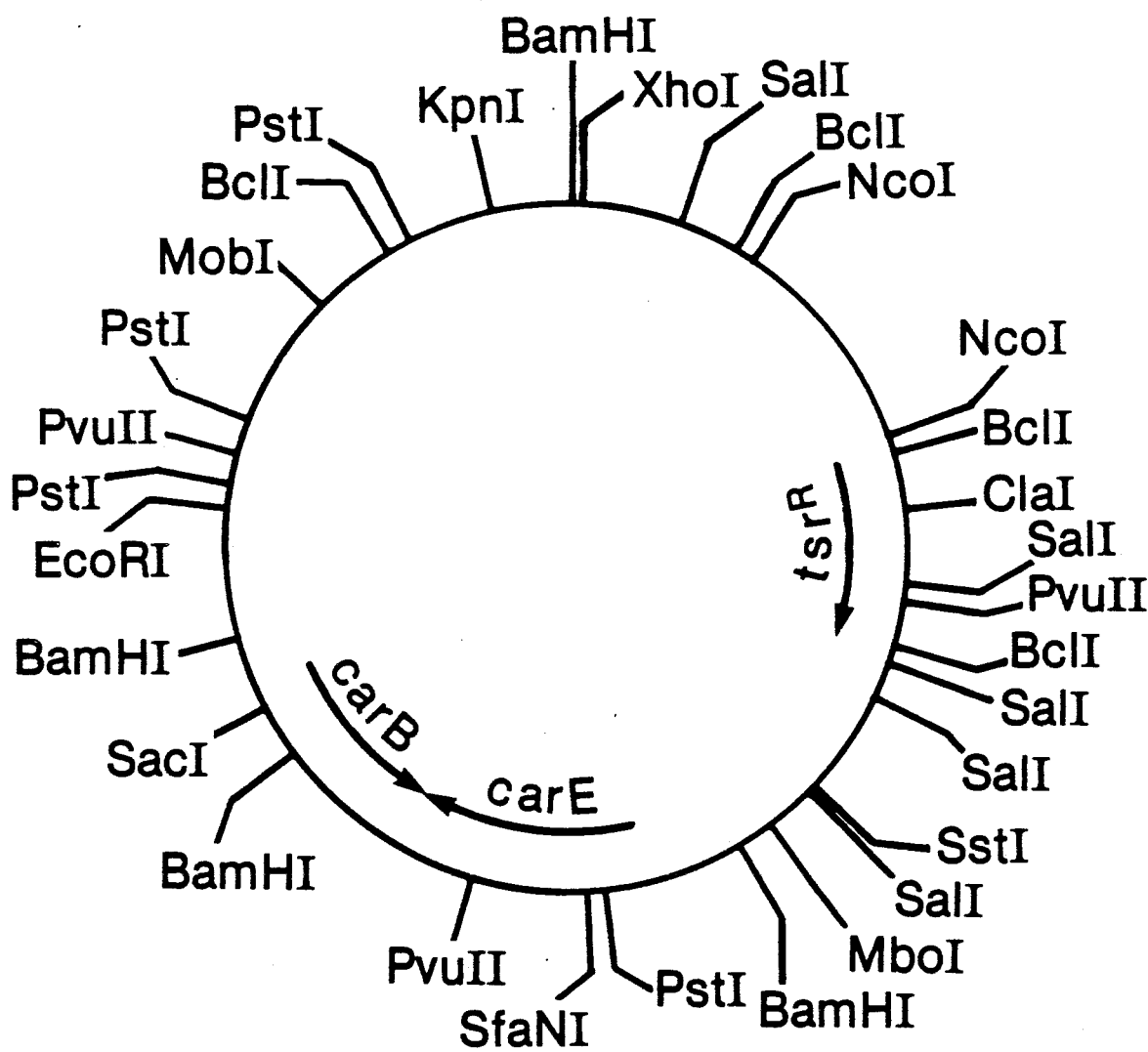
FIG. 4 is a restriction site and function map of plasmid pOJ159.

The carE gene can also be isolated from plasmid pOJ159, which contains a carbomycin resistance-conferring gene, designated carB, that is useful as a genetic marker in many organisms. Plasmid pOJ159 (FIG. 4) can be isolated from *Streptomyces griseofuscus* C581/pOJ159 (NRRL 18090) as described in Example 2. Plasmid pOJ159 was constructed by partially digesting genomic DNA of *Streptomyces thermotolerans* with restriction enzyme MboI, inserting the resulting DNA into BglII-digested plasmid pIJ702 (ATCC 39155), and identifying carbomycin-resistant Streptomyces transformants.

However, plasmid pOJ159 also contains a carE gene of the present invention. Because the carE gene was isolated from *Streptomyces thermotolerans*, the carE gene drives expression of acylase activity in *S. thermotolerans* and other host cells in which the promoter of the carE gene functions. Those skilled in the art will recognize that the intact carE gene of *S. thermotolerans* can be used to generate 4"-O-isovaleryl acylase activity in a variety of host cells, especially Streptomyces of any species.

The sequence of the carE gene is depicted below, beginning with the 5' end upstream of the coding sequence. This 5' noncoding sequence contains the promoter of the carE gene, another important aspect of the present invention. Only the sequence of the coding strand of the carE gene is depicted; the sequence of the non-coding strand can be obtained using the well-known rules of base-pairing: A pairs with T, and C pairs with G. The amino acid residue sequence of the carE gene product is also depicted below, beginning with the amino-terminal end; each amino acid residue is located below the DNA encoding that residue. Both the DNA and amino acid residue sequences are numbered to facilitate an understanding of the invention.

NUCLEOTIDE SEQUENCE OF THE carE GENE AND AMINO ACID RESIDUE
SEQUENCE OF THE carE GENE PRODUCT

```
              10                  30                  50
5'-GGATCCGGCC ACGAAGTGGT GGAGGTTCTG GTCCGCGGCG CCTTCACCGA 70                  90
   CGAACGCGGC GAGGTTGCGG GCGGTCTTGC GTCCCTGAGC GGTGAGCAGA 110                 130                 150
   CCACGGACGT ACTGTTCGCC CCTCTTGCGC TGGTCGGCCC GGCGCAGCGA 170                 190
   ACTGAACAGC TCCGAGCAGG TCTCGGAGAT GTGCGTATCG AAGTCGTCAT 210                 230                 250
   GGACACCGGT GTCCCACATG GAGGCCGACG GTTTTGAGCC ACACGGAATA 270                 290
   CTGTGCACTA TGACCCTCAC AAGCCGCTTG ATCCACTGGA AAAGACCTGC 310                 330                 350
   TGGCCAGCCT CAGTTAATCC GTTCCGTAAA TCCAGGTGCC GAGGCCACAC 370                 390
   AATTCTTCCC GCACACCTCG CGTCACACCG CCGCGAAGAA CCGTCGTCCG 410                 430                 450
   TGTTTCCGGA TGATTAAATC CGCGTCGCCC GGTGACGAAA CCACCGTCGC
```

-continued
NUCLEOTIDE SEQUENCE OF THE carE GENE AND AMINO ACID RESIDUE
SEQUENCE OF THE carE GENE PRODUCT

```
                      470                   490
         CGGCCGTGCA GCGGTGGGAA CACACCACTG TCGCGCGGCG 510                   530
         GCTCACACTC TTTGTCAGAT ACGCCTTGCC CGCGGCCGCG 550                   570
         CGGTGCCTTA GACATCTGCT CCCACCCACC CGTCCGCCGC GAGGTCACCC ATG
                                                                 Met
                                                                  1

590                          610
         CCC CTG CCG AAA CAT CTT CCC GCG CTC GGC GGG ATG CGT TTC ATC
         Pro Leu Pro Lys His Leu Pro Ala Leu Gly Gly Met Arg Phe Ile
                      5               10                      15

630                     650                     670
         TCC GCT CTA CTG GTA TTC ACC TCC CAT ATA TCG ACA CAG CCG TTC
         Ser Ala Leu Leu Val Phe Thr Ser His Ile Ser Thr Gln Pro Phe
                      20                  25                  30

690                     710
         TTC AAG AAC ACC GAG ATC AAT TCC GCG CTG CAG TTC CCG CTG AAC
         Phe Lys Asn Thr Glu Ile Asn Ser Ala Leu Gln Phe Pro Leu Asn
                      35                  40                  45

730                     750
         CGG CTG GGC CCG CTG ACG GTC TCG TTC TTC TTC ATG CTC AGC GGT
         Arg Leu Gly Pro Leu Thr Val Ser Phe Phe Phe Met Leu Ser Gly
                      50                  55                  60

770                     790
         TTC GTC CTC ACC TGG GCG GGT CTG CCC GAC AAG TCC AAG GTG AAC
         Phe Val Leu Thr Trp Ala Gly Leu Pro Asp Lys Ser Lys Val Asn
                      65                  70                  75

810                     830                         850
         TTC TGG CGG CGG CGC ACG GTC CGC GCG TAC TCG CTG CAC CTG CCC
         Phe Trp Arg Arg Arg Thr Val Arg Ala Tyr Ser Leu His Leu Pro
                      80                  85                  90

870                     890
         GTG CTG CTG GTG ACG CTG CTG ATC GTG CTG GCC CTC AAC GAG CCC
         Val Leu Leu Val Thr Leu Leu Ile Val Leu Ala Leu Asn Glu Pro
                      95                  100                 105

910                         930
         AAC ATG GGC CGA TCG GTG TGG GAC GGA CTG CTC ACG AAC CTG CTG
         Asn Met Gly Arg Ser Val Trp Asp Gly Leu Leu Thr Asn Leu Leu
                      110                 115                 120

950                         970
         CTG ATC CAG GCA TGG TTC CCC GAC CAC CAC GAG TAC GGC AGC ATG
         Leu Ile Gln Ala Trp Phe Pro Asp His His Glu Tyr Gly Ser Met
                      125                 130                 135

990                         1010                    1030
         AAC CCG GTG GCG TGG TCG CTC TCC TGC GAG CTG TTC TTC TAC GCC
         Asn Pro Val Ala Trp Ser Leu Ser Cys Glu Leu Phe Phe Tyr Ala
                      140                 145                 150

1050                    1070
         ATG TTC CCG TTC CTC TTC GCC TTC TTC ACC AAG GTC CGT ACG GAC
         Met Phe Pro Phe Leu Phe Ala Phe Phe Thr Lys Val Arg Thr Asp
                      155                 160                 165

1090                    1110
         CGG CTC TGG CGG TGG GCC GCC GCG GTG TCC GTG GCC GCC GTC TCC
         Arg Leu Trp Arg Trp Ala Ala Ala Val Ser Val Ala Ala Val Ser
                      170                 175                 180

1130                    1150
         ATC CCC CTG GTC GCA CTG CTG CTG CCG GCC AGC CCG CCC CTG CCG
         Ile Pro Leu Val Ala Leu Leu Leu Pro Ala Ser Pro Pro Leu Pro
                      185                 190                 195
```

-continued
NUCLEOTIDE SEQUENCE OF THE carE GENE AND AMINO ACID RESIDUE
SEQUENCE OF THE carE GENE PRODUCT

```
      1170                            1190                          1210
TGG   GAC   CCG   GAC   ATG   CCG   CAG   CTG   CGG   TGG   TGG   TTC   ATC   TAC   ATG
Trp   Asp   Pro   Asp   Met   Pro   Gln   Leu   Arg   Trp   Trp   Phe   Ile   Tyr   Met
                  200                       205                           210

1230                            1250
TTC   CCG   CCG   GTG   CGG   CTG   CTG   GAG   TTC   GTG   CTC   GGG   ATG   CTC   ATG
Phe   Pro   Pro   Val   Arg   Leu   Leu   Glu   Phe   Val   Leu   Gly   Met   Leu   Met
                  215                       220                           225

1270                                  1290
GCC   CAG   ATC   GTG   ATC   CGG   GGA   CGC   TGG   AGG   GGC   CCG   CGT   CCC   CTG
Ala   Gln   Ile   Val   Ile   Arg   Gly   Arg   Trp   Arg   Gly   Pro   Arg   Pro   Leu
                  230                       235                           240

1310                                  1330
GCC   TGC   GTC   GCG   CTG   TTC   TCA   GCG   GTG   TTC   GCG   GTG   ACG   TTC   GCG
Ala   Cys   Val   Ala   Leu   Phe   Ser   Ala   Val   Phe   Ala   Val   Thr   Phe   Ala
                  245                       250                           255

1350                                  1370                          1390
GTG   CCG   AAC   CAC   TAC   GAC   CCC   GGC   GCG   TTG   ACC   GTC   CCG   GTG   ATC
Val   Pro   Asn   His   Tyr   Asp   Pro   Gly   Ala   Leu   Thr   Val   Pro   Val   Ile
                  260                       265                           270

1410                            1430
GCG   CTG   CTG   CTC   GCC   TCG   GTG   GCC   GTC   GGT   GAT   GTG   CGC   GGC   GTC
Ala   Leu   Leu   Leu   Ala   Ser   Val   Ala   Val   Gly   Asp   Val   Arg   Gly   Val
                  275                       280                           285

1450                                  1470
CGC   TCC   TGG   CTG   GGG   ACC   AGG   ACG   ATG   GTG   CTG   CTG   GGG   GAA   CTC
Arg   Ser   Trp   Leu   Gly   Thr   Arg   Thr   Met   Val   Leu   Leu   Gly   Glu   Leu
                  290                       295                           300

1490                                  1510
ACC   TTC   GCC   TTC   TAC   CTC   GTG   CAC   TAC   CTG   ATC   ATC   CAG   TAC   GGG
Thr   Phe   Ala   Phe   Tyr   Leu   Val   His   Tyr   Leu   Ile   Ile   Gln   Tyr   Gly
                  305                       310                           315

1530                            1550                                1570
CAC   CGC   TTC   GCC   GGC   GGG   AAG   CAG   GGC   TAT   TAC   CGG   CAG   TGG   GAC
His   Arg   Phe   Ala   Gly   Gly   Lys   Gln   Gly   Tyr   Tyr   Arg   Gln   Trp   Asp
                  320                       325                           330

1590                                  1610
ACA   CCG   GCC   GCC   GTC   GGG   CTG   ACC   CTG   CTC   GCC   TTC   ACG   CTG   GCG
Thr   Pro   Ala   Ala   Val   Gly   Leu   Thr   Leu   Leu   Ala   Phe   Thr   Leu   Ala
                  335                       340                           345

1630                                  1650
CTG   GGG   CTG   TCG   GCG   TTC   CTG   CAC   TTC   TTC   GTG   GAG   AAG   CCG   GTC
Leu   Gly   Leu   Ser   Ala   Phe   Leu   His   Phe   Phe   Val   Glu   Lys   Pro   Val
                  350                       355                           360

1670                                  1690
ATG   CGA   ACC   CTG   GGA   CGG   CCG   CGG   CGG   TCC   CCG   GAC   GCC   GGC   TCG
Met   Arg   Thr   Leu   Gly   Arg   Pro   Arg   Arg   Ser   Pro   Asp   Ala   Gly   Ser
                  365                       370                           375

1710                            1730                                1750
ACA   CCC   AGG   TCC   GAA   CCC   GCC   CCG   TCC   GGC   ACT   CCG   TAG   CCG   ACG
Thr   Pro   Arg   Ser   Glu   Pro   Ala   Pro   Ser   Gly   Thr   Pro
                  380                       385

1770                          1790
CGG   GAC   GAC   CGG   TGC   GCG   GCG   CGC   CCT   CGG   GCG   CGC   CCC   GCA   CCG 1810                            1830
GTG   TGC   GTC   AGC   GCC   CGT   GGA   GTT   CCT   CGA   AGA   GTG   TGA   TCC   ATT

1850
GGC   CCG   GG-3'
```

In the sequence above, A is deoxyadenyl, G is deoxyguanyl, C is deoxycytidyl, T is thymidyl, Ala is an alanine, Arg is an arginine, Asn is an asparagine, Asp is an aspartic acid, Cys is a cysteine, Gln is a glutamine, Glu is a glutamic acid, Gly is a glycine, His is a histidine, Ile is an isoleucine, Leu is a leucine, Lys is a lysine, Met is a methionine, Phe is a phenylalanine, Pro is a proline, Ser is a serine, Thr is a threonine, Trp is a tryptophan, Tyr is a tyrosine, and Val is a valine.

Figure 2:
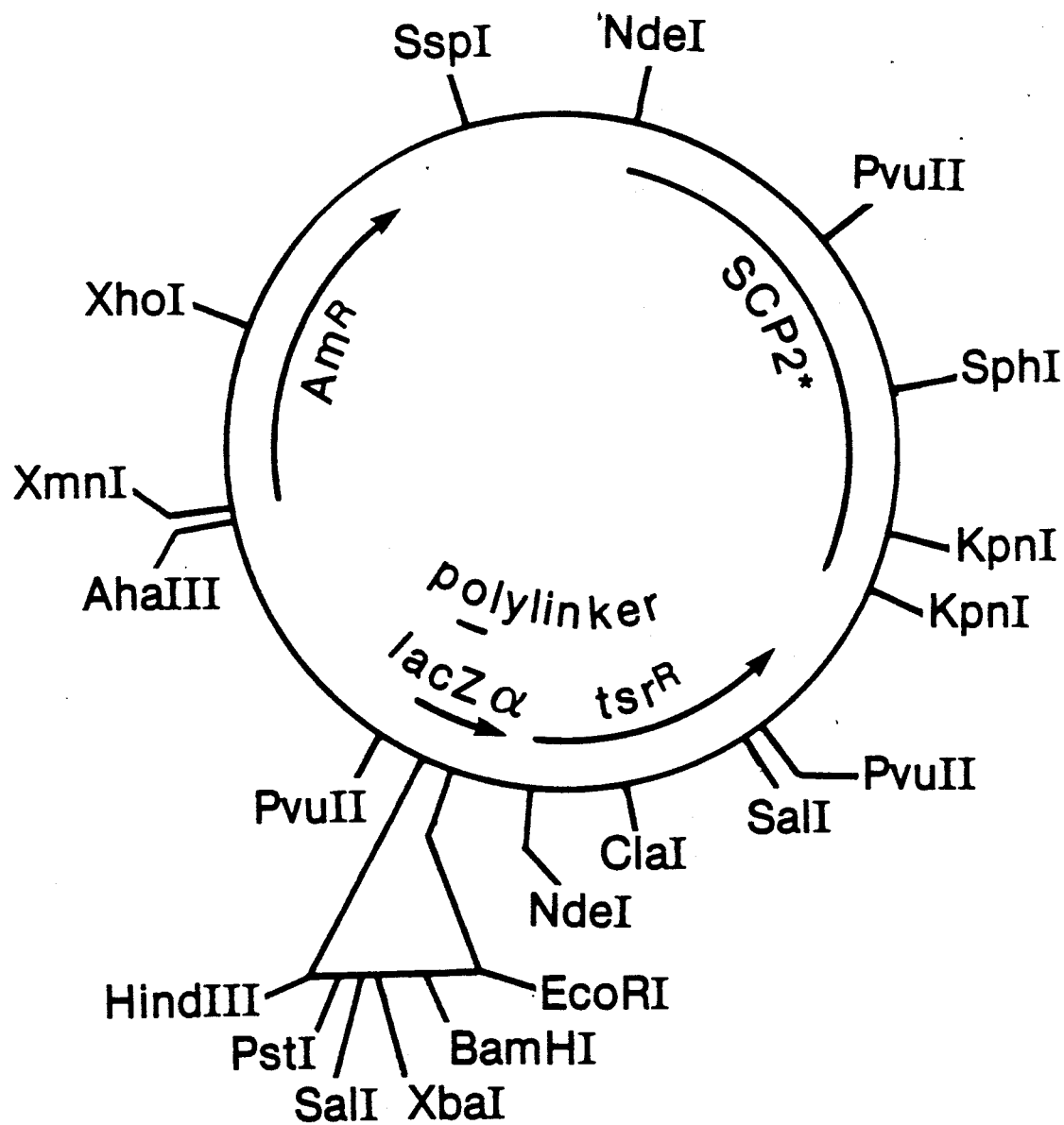
FIG. 2 is a restriction site and function map of plasmid pOJ160.
Figure 3:
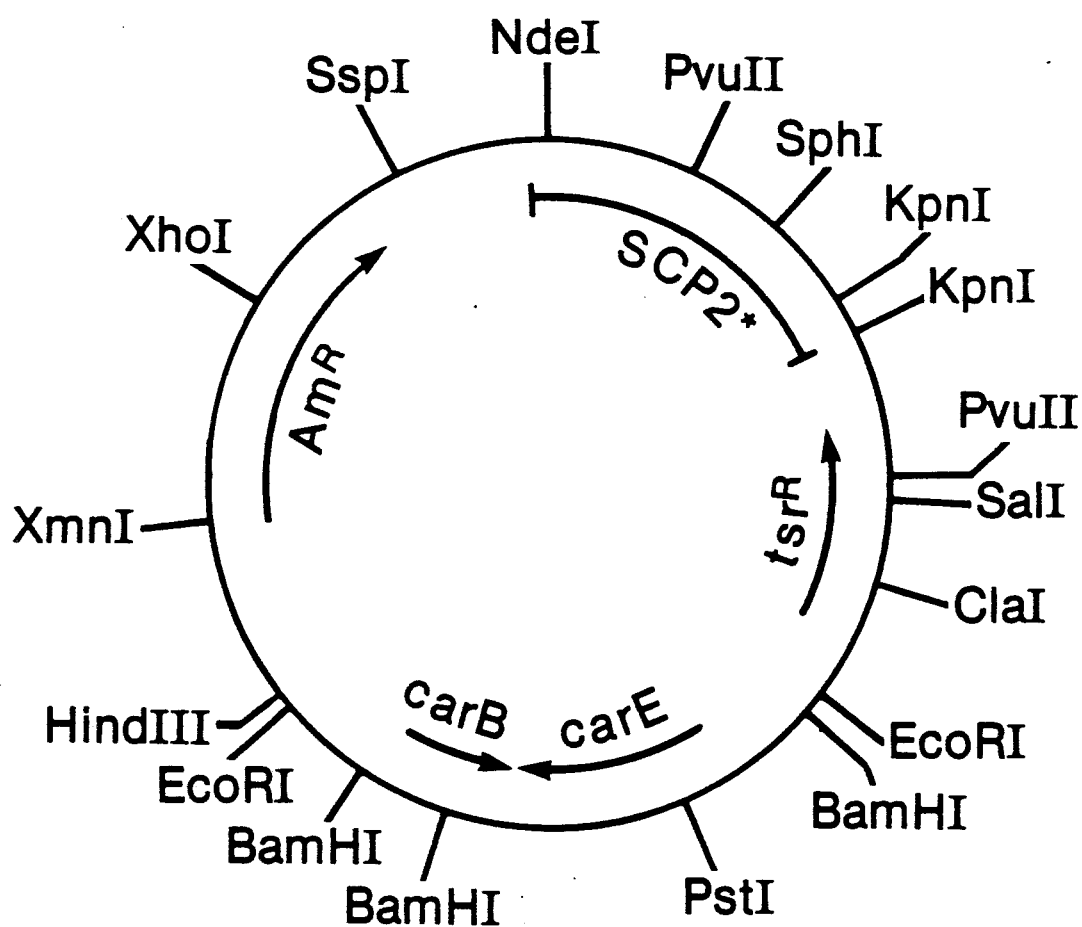
FIG. 3 is a restriction site and function map of plasmid pOJ313.

A variety of vectors of the invention can be readily constructed using either plasmid pOJ171 or pOJ159 as starting material. Vectors that comprise the intact carE gene are especially preferred for use in Streptomyces. For example, the ~3.8 kb, carE gene-containing, EcoRI restriction fragment of plasmid pOJ171 was isolated and inserted into EcoRI-digested plasmid pOJ160 (FIG. 2 and NRRL B-18088) to yield plasmids pOJ313 (FIG. 3) and pOJ313A, which differ only with respect to the orientation of the ~3.8 kb EcoRI restriction fragment. The construction protocol for plasmids pOJ313 and pOJ313A is given in Example 3.

Figure 5:
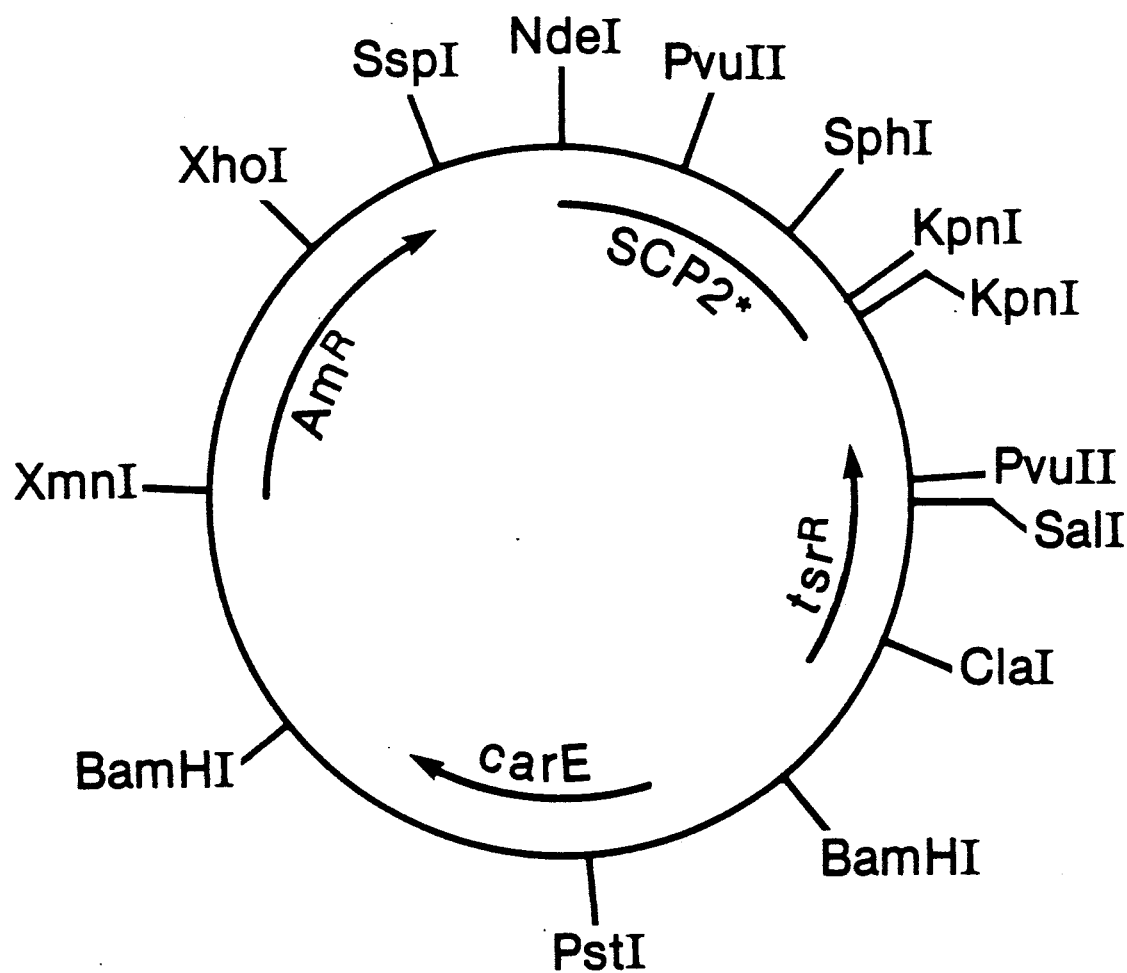
FIG. 5 is a restriction site and function map of plasmid pOJ230.

Plasmid pOJ230 (FIG. 5) of the invention was derived from plasmid pOJ159 by ligating the ~2.4 kb, carE gene-containing BamHI restriction fragment of plasmid pOJ159 to BamHI-digested plasmid pOJ160, as described in Example 4. Because this fragment could insert in either of two orientations, the ligation produced two plasmids, designated pOJ230 and pOJ231, that differ only with respect to the orientation of the ~2.4 kb, carE-containing, BamHI restriction fragment.

Vectors of the present invention that contain the intact carE gene are preferred for use in increasing the 4"-O-isovaleryl transferase activity in organisms that biosynthesize carbomycin or other macrolide antibiotics. Consequently, Streptomyces, especially species that produce an antibiotic that contains a mycarose or related sugar, are preferred host cells for vectors of the invention that contain the intact carE gene. Of course, the carE gene can be reconstructed using recombinant DNA techniques for purposes of producing the carE gene product in any host cell.

Illustrative vectors of the present invention were introduced into Streptomyces ambofaciens for purposes of exemplifying the use of the intact carE gene to increase the 4"-O-isovaleryl acylase activity of an organism. S. ambofaciens produces spiramycin and a variety of other spiramycin-related compounds that contain a mycarose residue with a 4"-OH group. S. ambofaciens does not naturally produce a 4"-O-isovaleryl acylase activity. Plasmids pOJ159, pOJ171, pOJ230, pOJ231, and pOJ313 have been used to transform S. ambofaciens, as described in Example 5. The resulting transformants produce isovaleryl spiramycin due to the presence of the acylase-encoding recombinant DNA vector.

Similarly, when plasmids pOJ159 and pOJ313 were used to transform Streptomyces lividans TK23 (NRRL 15826), the resulting transformants could not only grow in the presence of higher levels of spiramycin (due to the carB gene product) but also converted the spiramycin to isovaleryl spiramycin. A transformation protocol for S. lividans is set forth in Example 6.

Vectors of the invention are thus generally useful to acylate the mycarose residues of macrolide antibiotics such as spiramycin and carbomycin. Streptomyces fradiae produces tylosin, another macrolide antibiotic that contains a mycarose residue. U.S. Pat. No. 4,092,473 describes a 4" acylation of the mycarose residue of tylosin to produce isovaleryl tylosin, an important antibiotic. U.S. Pat. No. 4,656,258 describes the production of isovaleryl macrocin. The 4"-OH group of mycarose is not acylated in tylosin or its intermediates, but recombinant DNA vectors of the present invention can be used to transform a tylosin-producing cell into a cell that produces 4"-acylated tylosin and 4"-acylated tylosin intermediates.

The intact carE gene isolated from Streptomyces thermotolerans expressed well in S. ambofaciens and S. lividans. Yet even if the original carE gene failed to express in a given organism, such as E. coli, because, for example, the Streptomyces promoter of the carE failed to function in that organism, the carE coding sequence of the present invention could be ligated to a DNA fragment containing an appropriate promoter, ribosome-binding site or other regulatory element to achieve expression of the carE gene in the host of choice. This technique is illustrated in the construction of an E. coli expression vector of the invention, designated pOJ235 and more fully described below.

Plasmids pOJ159, pOJ171, pOJ230, pOJ231, pOJ313, and pOJ313A contain the intact carE gene: (1) a promoter that directs transcription of the protein-coding sequence; (2) a sequence that, when transcribed into mRNA, directs translation of the transcript; (3) a protein-coding sequence; and (4) a transcription terminator. Each of these elements is independently useful and can, through the techniques of recombinant DNA technology, be used to form recombinant genes of great variety. The DNA sequence of the carE gene, provided above, reveals the location of the carE coding sequence and thus allows one to position other promoters, for example, the trp, lpp, and lac promoters of E. coli, the hybrid tac promoter, the λpL promoter, and the veg promoter of Bacillus, in reading phase with the carE coding sequence. By choosing the proper promoter, one can construct vectors that drive expression of the carE gene product in any host cell. The promoter of the carE gene of Streptomyces thermotolernas is useful in its own right. The promoter and other regulatory elements of the carE gene can be linked to any coding sequence to produce useful recombinant genes. Thus, the individual elements of the carE gene, both the promoter and coding sequence, comprise important components of the present invention.

The promoter of the carE gene is contained within nucleotides 1 to 580 in the carE gene sequence depicted above. This sequence also contains the sequence 5'-CCGTCCGCCG-3' (see sequence around nucleotide number 570), which is present in a number of antibiotic biosynthetic and antibiotic resistance-conferring genes. The sequence 5'-CCGTCCGCCG-3' and closely related sequences, such as 5'-CCGTCCCGCCG-3', are believed to be important in the regulation of such genes and thus can be used as a probe to detect antibiotic biosynthetic and antibiotic resistance-conferring genes.

Those skilled in the art will recognize that the carE sequence deposited under accession number NRRL B-18169 and NRRL 18090 can be used to prepare DNA probes for use in obtaining other biosynthetic gene-containing DNA segments, especially segments encoding macrolide biosynthetic genes. In addition, due to the diversity of Streptomyces thermotolerans strains both in nature and also in the laboratory, there will be a variety of allelic variants of the carE gene that can be readily isolated given the carE gene-containing compounds of this invention. These allelic variants, which encode gene products with an amino acid residue sequence that differs from that of the carE gene product, are functionally equivalent to the carE gene of the present invention.

For example, those skilled in the art will recognize that the carE gene from the improved bioconverting strain of Streptomyces thermotolerans NRRL 15270 described in U.S. Pat. No. 4,522,919 can be isolated on an ~2.4 kb BamHI restriction fragment as follows. BamHI restriction fragments are generated from genomic DNA isolated from the NRRL 15270 strain and inserted into BamHI-digested plasmid pOJ160. This procedure yields a genomic library of *S. thermotolerans* NRRL 15270, and this library can be transformed into *E. coli* and the resulting transformants probed by colony hybridization using the ~2.4 kb, carE-containing, BamHI restriction fragment of, for example, plasmid pOJ230 as a hybridization probe. Plasmid DNA isolated from colonies that hybridize in the procedure contains the ~2.4 kb, carE-containing, BamHI restriction fragment of *S. thermotolerans* NRRL 15270. The carE gene of *S. thermotolerans* NRRL 15270 and the coding sequence of that gene are important compounds of the present invention, because the carE gene product of the NRRL 15270 strain is believed to have a different substrate specificity than the carE gene product of wild-type *S. thermotolerans*. Analogous procedures can be used to generate carE-containing DNA from any organism that contains carE-encoding DNA.

A variety of known Streptomyces replicons can be used in conjunction with the carE gene to construct expression vectors of the present invention. Table I is an illustrative, but not comprehensive, listing of Streptomyces plasmids from which Streptomyces replicons can be obtained. Those skilled in the art recognize that, so long as the replicon function is not disrupted, all or part of the plasmids can be used to construct vectors that contain the carE gene of the present invention. The plasmid-containing host and depository accession number are also listed in Table I.

TABLE I

| Streptomyces Plasmids | | |
|---|---|---|
| Plasmid | Host | Accession Number |
| SCP2 | *Streptomyces coelicolor* A3(2) | NRRL 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | Streptomyces 3022A | NRRL 11441 |
| SLP1 | *Streptomyces lividans* | NCIB* 11417 |
| pNM100 | *Streptomyces virginiae* | NRRL 15156 |
| pEL103 | *Streptomyces granuloruber* A399 12.13/pEL103 | NRRL 12549 |
| pIJ702 | *Streptomyces lividans* | ATCC 39155 |

*National Collection of Industrial Bacteria (NCIB), Torry Research Station, Post Office Box 31, 135 Abbey Road, Aberdeen AB98DG, Scotland, United Kingdom.

Restriction fragments used to construct vectors illustrative of the present invention can be conventionally modified to facilitate ligation. For example, molecular linkers can be provided to a particular carE biosynthetic gene-containing restriction fragment or to DNA comprising vector replication or integration functions. Thus, specific sites for subsequent ligation can be conveniently constructed. In addition, the various carE biosynthetic gene-containing restriction fragments or sequences that provide for replication or chromosomal integration of a given vector can be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose. Thus, a myriad of DNA sequences that encode the carE gene product can be constructed. It is also noteworthy that a given carE biosynthetic gene-containing restriction fragment is not limited to a particular position on a cloning vector, as long as critical, vector-controlled functions are not disrupted. Those skilled in the art understand or can readily determine which sites on a vector are advantageous for the ligation or insertion of a particular carE gene-containing restriction fragment.

Of course, the carE gene or coding sequence can be used to construct vectors other than plasmids. Phage φC31 is a well-known Streptomyces phage that is an excellent source of starting material for constructing integrative carE gene-containing vectors that further exemplify the present invention. A derivative of phage φC31, plasmid pKC331, is especially preferred for constructing such integrating vectors and can be obtained from *E. coli* K12 BE447/pKC331 (NRRL B-15828). φC31-type phages are integrative vectors and can be readily modified to incorporate the carE gene and thus confer 4"-O-isovaleryl acylase activity to Streptomyces. Even plasmids that contain a replicon that provides for extrachromosomal maintenance of the plasmid sometimes integrate into the genome of the host cell, usually with concomitant deletion of the replicon sequences. The present invention thus is not limited by the type of vector used to introduce the carE gene or coding sequence into the target host cell nor by the location of the carE gene or coding sequence once introduction has occurred.

Vectors of the present invention preferred for Streptomyces contain a Streptomyces replicon and a carE gene-containing restriction fragment. Because amplification and manipulation of plasmids is done faster and more efficiently in *E. coli* than in Streptomyces, it is convenient to add DNA sequences that also allow for replication in *E. coli*. Thus, the addition of functional replicon-containing and antibiotic resistance-conferring restriction fragments from *E. coli* plasmids such as, for example, pUC8, pUC18, pUC19, pBR322, pACYC184, pBR325, pBR328, and the like is highly advantageous and adds to the general utility of the present illustrative vectors.

Figure 6:
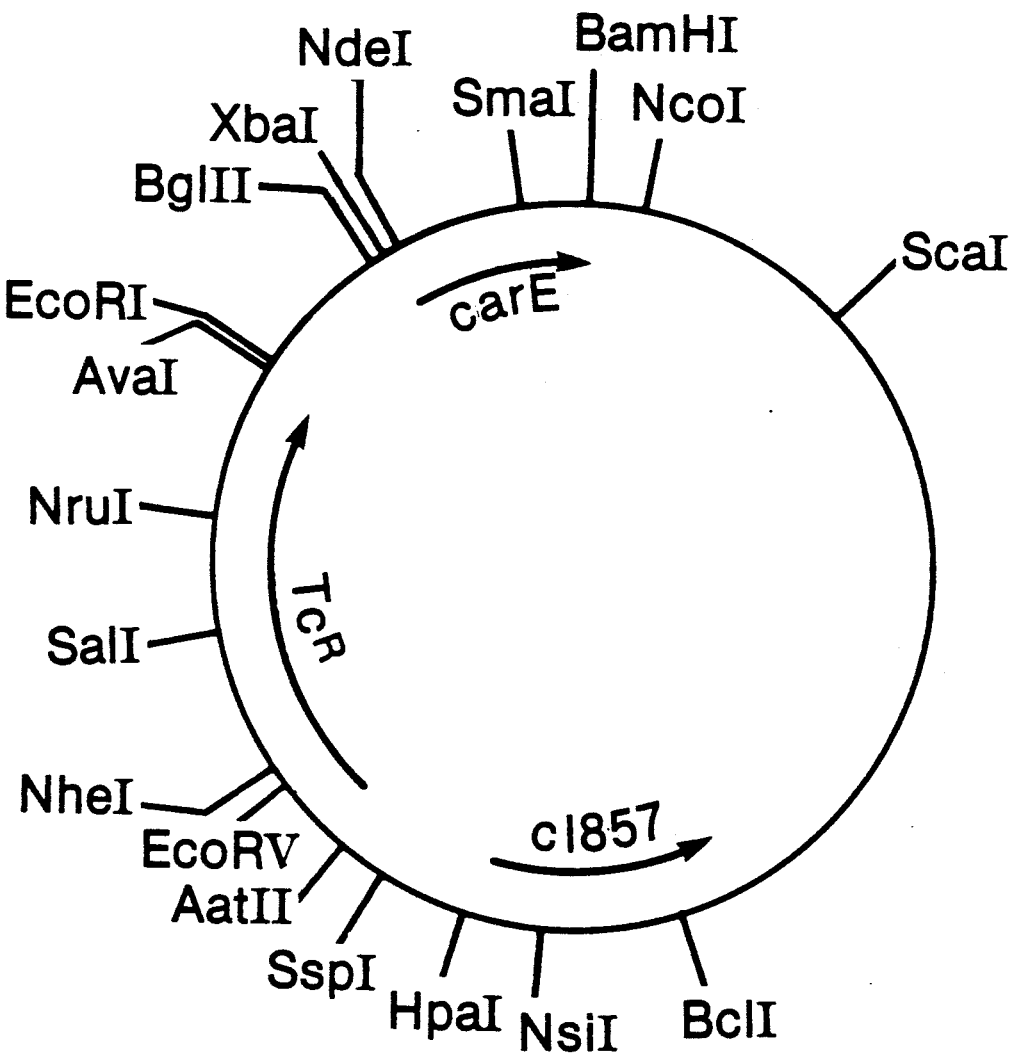
FIG. 6 is a restriction site and function map of plasmid pOJ235.

The present invention provides 4"-O-isovaleryl acylase expression vectors that not only contain *E. coli* replicons but also contain recombinant *E. coli* carE genes. The recombinant *E. coli* carE gene contains a promoter that functions in *E. coli* positioned to drive expression of the carE gene product. Illustrative plasmid pOJ235 (FIG. 6) of the invention can be constructed as described in Example 7. Plasmid pOJ235 drives expression of the carE gene product in *E. coli* and contains the carE coding sequence under the control of the λpL promoter, itself regulated by a temperature-sensitive cI857 gene product also encoded on the plasmid.

Those skilled in the art recognize that the carE gene, its coding sequence, and its promoter can be individually combined with a variety of other DNA compounds to create useful 4"-O-isovaleryl acylase and other expression vectors of the invention. For instance, *Streptomyces thermotolerans* contains two carbomycin resistance-conferring genes, designated carA and carB. These two carbomycin resistance genes may act in concert to cause high-level resistance in *Streptomyces thermotolerans*. The present invention also provides vectors that contain the carE gene and either or both of the carA and carB genes. Plasmid pOJ171, for example, comprises both the carE and carB genes. Plasmid pOJ171 also encodes carG, which encodes an activity involved in the biosynthesis of the lactone ring of carbomycin in *S. thermotolerans*.

The cloning vectors and transformants of the present invention provide for the cloning of genes to improve and alter yields of various products that are currently produced in Streptomyces and related cells. Examples of such products include, but are not limited to, carbomycin, tylosin, erythromycin, and the like. The present invention also provides selectable vectors that are useful for cloning, characterizing, and reconstructing a variety of useful DNA sequences.

Streptomyces transformants of the invention can be cultured in a number of ways using any of several different media. Preferred carbohydrate sources in a culture medium include, for example, molasses, glucose, dextrin, and glycerol. Nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for constructing the invention are described where appropriate.

EXAMPLE 1

Isolation of Plasmid pOJ171

A. Culture of *E. coli* K12 SF8/pOJ171

Plasmid pOJ171 can be obtained from the Northern Regional Research Center in *E. coli* K12 SF8 under the accession number NRRL B-18169. The lyophils of *E. coli* K12 SF8/pOJ171 are plated onto L-agar plates containing 200 µg/ml apramycin to obtain a single colony isolate of the strain. This colony is used to inoculate about 500 ml of L broth containing 200 µg/ml apramycin, and the resulting culture is incubated at 37° C. with aeration until the cells reach stationary phase.

Plasmid DNA was obtained from the cells to use in construction of plasmid pOJ313 in accordance with the following procedure, which is adapted from Maniatis et al., 1982, *Molecular Cloning* (Cold Spring Harbor Laboratory). This same procedure was used, but on a smaller scale and with the ultracentrifugation steps replaced with phenol followed by chloroform extractions, to prepare the plasmid DNA used to identify the *E. coli* K12 RR1ΔM15/pOJ313 transformants.

About 500 ml of stationary-phase *E. coli*/pOJ171 cells are harvested by centrifugation at 4000Xg for 10 minutes at 4° C., and the supernatant is discarded. The cell pellet is washed in 100 ml of ice-cold STE buffer (0.1 M NaCl; 10 mM Tris-HCl, pH 7.8; and 1 mM EDTA). After the cell pellet is washed, the pellet is resuspended in 10 ml of Solution 1 (50 mM glucose; 25 mM Tris-HCl, pH=8.0; and 10 mM EDTA) that contains 1 mg/ml lysozyme and is left at room temperature for 10 minutes. Twenty ml of Solution 2 (0.2 N NaOH and 1% SDS) are then added to the lysozyme-treated cells, and the solution is gently mixed by inversion. The mixture is incubated on ice for 10 minutes.

Fifteen ml of ice-cold, 3 M sodium acetate, pH=4.8, are added to the lysed-cell mixture, and the solution is mixed by inversion. The solution is incubated on ice for 60 minutes. The 3 M sodium acetate solution is prepared by mixing equal volumes of 3 M acetic acid and 3 M sodium acetate.

The lysed cell mixture is centrifuged in an ultracentrifuge at 20,000 rpm for 20 minutes at 4° C. About 36 ml of supernatant are recovered, and 2.5 volumes of ethanol are added, mixed, and the resulting solution left on ice for 15 minutes. The plasmid DNA is collected by centrifugation at 12,000Xg for 30 minutes at room temperature. The supernatant is discarded, and the DNA pellet is washed with 70% ethanol at room temperature. The ethanol wash is decanted, and the pellet is dried in a vacuum desiccator. The pellet is then resuspended in 8 ml of TE buffer (10 mM Tris-HCl, pH=8.0, and 1 mM EDTA).

Eight grams of CsCl are added to the DNA solution. About 0.8 ml of a 10 mg/ml solution of ethidium bromide in water are added for each 10 ml of CsCl-DNA solution. The final density of the solution is about 0.761 g/ml, and the ethidium bromide concentration is about 800 µg/ml. The solution is transferred to an ultracentrifuge tube, filled to the top with TE buffer containing 0.761 g of CsCl per ml, sealed, and centrifuged at 45,000 rpm for 24 hours at 20° C. After centrifugation, two bands of DNA are visible in ordinary light and become even more prominent in UV light. The cap is removed from the tube, and the lower DNA band is recovered using a syringe with a #21 hypodermic needle inserted through the side of the centrifuge tube.

The ethidium bromide is removed from the solution of plasmid DNA by several extractions with water-saturated 1-butanol, and the CsCl is removed by dialysis against TE buffer. After extractions with buffered phenol and then chloroform, the DNA is precipitated, washed with 70% ethanol, and dried. About 0.5 mg of plasmid pOJ171 DNA can be obtained by this procedure. A restriction site and function map of plasmid pOJ171 is presented in FIG. 1 of the accompanying drawings.

EXAMPLE 2

Isolation of Plasmid pOJ159

A. Culture of *Streptomyces griseofuscus* C581/pOJ159

About $10^8$ spores of *Streptomyces griseofuscus* C581/pOJ159 (NRRL 18090) are inoculated into 10 ml of Trypticase Soy Broth (TSB is made at 30 g/L and is obtained from Baltimore Biological Laboratories (BBL), P.O. Box 243, Cockeysville, Md. 21031) containing 25 µg/ml thiostrepton and grown at 29° C. until the culture is in early stationary phase. The culture was then homogenized, and 5 ml of the homogenized culture were used to inoculate 100 ml of TSB also containing thiostrepton. The 100 ml of culture were incubated at 29° C. until the *Streptomyces griseofuscus* C581/pOJ159 cells reached stationary phase.

B. Plasmid Isolation

The cells were collected and washed once with a 10.3% sucrose solution. The cells were then suspended in 24 ml of 10.3% sucrose, and 6 ml of 5X lysozyme solution (125 mM Tris-HCl, pH=8; 125 mM Na$_2$EDTA, pH=8; 10 mg/ml lysozyme; and 10.3% sucrose) were added. The solution was mixed and then incubated at 30° C. for 30-60 minutes, and then, about 18 ml of a solution that was 0.3 M NaOH, 1% SDS, and prewarmed to 50° C. were added, mixed and the resulting mixture incubated at 80° C. for 10 minutes. The mixture was then cooled to room temperature, and 12 ml of a solution made by mixing 500 g phenol and 500 g CHCl$_3$ in 200 ml H$_2$O were added and mixed well with the cell-extract. The phases were separated by centrifugation at 6000-8000 rpm for 10 minutes; approximately 45 ml of the resulting upper phase were transferred to a clean bottle.

Next, 4.5 ml of 3 M NaOAc and 50 ml of isopropanol were added to the supernatant, and the solution was mixed and left at room temperature for 30 minutes. The solution was then centrifuged (8000 rpm for 30 minutes) and the resulting supernatant discarded. The pellet was resuspended in 10 ml of TE buffer (10 mM Tris-HCl, pH=8, and 1 mM EDTA) containing 9.5 g of CsCl. About 1 ml of a 5 mg/ml solution of ethidium bromide was added to the solution to bring the final volume to 12.5 ml. The solution was then centrifuged at 52,000 rpm for 48 hours at 20° C. in a fixed-angle ultracentrifuge rotor. The fraction containing the plasmid band was extracted 5 times with isopropanol saturated with 20X SSC (0.3 M NaCl and 0.3 M NaCitrate) to remove the ethidium bromide. After the extractions, the sample was dialyzed against 1000 volumes of H$_2$O and then against 1500 volumes of TE buffer. The procedure yields about 100 μg of plasmid pOJ159 DNA at a concentration of ~0.2 μg/μl and is stored at 4° C. A restriction site and function map of plasmid pOJ159 is presented in FIG. 4 of the accompanying drawings.

EXAMPLE 3

Construction of Plasmid pOJ313 and pOJ313A

A. Isolation of Plasmid pOJ160

Plasmid pOJ160 can be obtained from the Northern Regional Research Center in *E. coli* K12 JM109 under the accession number NRRL B-18088. The lyophils of *E. coli* K12 JM109/pOJ160 are plated onto L-agar plates containing 200 μg/ml apramycin to obtain a single colony isolate of the strain. This colony is used to inoculate about 500 ml of L broth containing 200 μg/ml apramycin, and the resulting culture is incubated at 37° C. with aeration until the cells reach stationary phase.

Plasmid DNA was obtained from the cells to use in construction of plasmid pOJ313 in accordance with the procedure set forth in Example 1, above. About 0.5 mg of plasmid pOJ160 DNA can be obtained by this procedure. A restriction site and function map of plasmid pOJ160 is presented in FIG. 2 of the accompanying drawings.

B. Final Construction of Plasmids pOJ313 and pOJ313A

About 10 μg (10 μl) of plasmid pOJ160 DNA were added to 2 μl of 10X EcoRI buffer (1.0 M Tris-HCl, pH=7.5; 0.5 M NaCl; 50 mM MgCl$_2$; and 1 mg/ml BSA), 6 μl of H$_2$O, and 2 μl (~30 units; unit definitions herein correspond to those of New England Biolabs, 32 Tozer Road, Beverly, Mass. 01915-9990, unless otherwise indicated) of restriction enzyme EcoRI. The resulting reaction was incubated at 37° C. for two hours. The EcoRI-digested plasmid pOJ160 DNA was collected by adjusting the sodium acetate (NaOAc) concentration of the reaction mixture to 0.30 M, adding 2.5 volumes of ethanol, chilling the reaction mixture to -70° C., and centrifuging to pellet the precipitated DNA. The pellet of EcoRI-digested plasmid pOJ160 DNA was resuspended in 400 μl of TE buffer (10 mM Tris-HCl, pH=8.0, and 1 mM EDTA). About 1 μl (0.1 unit) of bacterial alkaline phosphatase (International Biotechnology, Inc., P.O. Box 1565, New Haven, Conn. 06506) was added to the DNA solution, and the reaction was incubated at 65° C. for 1 hour. The reaction mixture was extracted with 400 μl of a 1:1 solution of phenol:chloroform and then extracted with 400 μl of chloroform. The EcoRI-digested, dephosphorylated plasmid pOJ160 DNA was collected by ethanol precipitation and centrifugation as described above, and the DNA pellet was resuspended in 10 μl of TE buffer.

About 10 μg of plasmid pOJ171 in 100 μl of TE buffer were added to 13 μl of 10X EcoRI buffer, 13 μl of H$_2$O, and 4 μl (~60 units) of restriction enzyme EcoRI. The resulting reaction was incubated at 37° C. for 2 hours. The reaction mixture was extracted, and the DNA was collected as described above. The DNA pellet was redissolved, loaded onto an agarose gel, and about ~0.5 μg of the desired ~3.8 kb, carE-containing, EcoRI restriction fragment of plasmid pOJ171 were purified from the gel and prepared for ligation.

The EcoRI-digested, dephosphorylated plasmid pOJ160 DNA (1 μl) was added to 10 μl (~0.5 μg) of the ~3.8 kb EcoRI restriction fragment, 2 μl of 10X ligase buffer (660 mM Tris-HCl, pH=8; 66 mM MgCl$_2$; 10 mM dithiothreitol (DTT); and 10 mM ATP), and 6 μl of H$_2$O. About 1 μl (~100 units) of T4 DNA ligase was added to the solution of DNA, and the resulting reaction was incubated at 15° C. overnight (~16 hours). The ligated DNA contained the desired plasmid pOJ313; a restriction site and function map of plasmid pOJ313 is presented in FIG. 3 of the accompanying drawings. Because the ~3.8 kb, carE gene-containing EcoRI restriction fragment of plasmid pOJ171 could insert into plasmid pOJ160 in either of two orientations, the ligation also produced plasmid pOJ313A, which differs from plasmid pOJ313 only with respect to the orientation of the carE gene-containing, EcoRI restriction fragment.

The EcoRI site on plasmid pOJ160 resides within a polylinker that itself forms part of the DNA sequence encoding the lacZ α-fragment. Expression of the lacZ α-fragment in an *E. coli* ΔM15 strain, such as *E. coli* K12 RR1ΔM15 (NRRL B-15440), restores the strain's ability to produce a functional β-galactosidase enzyme. Thus, plasmid pOJ160 can restore β-galactosidase activity to the *E. coli* K12 RR1ΔM15 strain. However, insertion of DNA into a restriction site of the polylinker linker on plasmid pOJ160, as occurs in the construction of plasmid pOJ313, disrupts the lacZ α-fragment coding sequence and concomitantly destroys the ability of the plasmid pOJ160 derivative to complement the ΔM15 mutation. β-galactosidase can hydrodyze X-Gal, which is 5-bromo-4- chloro-3-indolyl-β-D-galactopyranoside, a colorless compound, to an indigo-colored product and thus allows for a convenient screening method for discriminating between transformants containing starting plasmid pOJ160 and those containing a plasmid pOJ160 derivative, such as plasmid pOJ313.

To prepare *E. coli* K12 RR1ΔM15 cells that are competent for transformation, the lyophils of *E. coli* K12 RR1ΔM15 obtained from the NRRL are reconstituted to isolate single colonies. One single-colony isolate of RR1ΔM15 was inoculated into 10 ml of L broth, and the culture was incubated at 37° C. overnight with aeration. The overnight culture was used to inoculate 200 ml of L broth to yield a culture with an $O.D._{600}$ of about 0.1. The culture was incubated at 37° C. with aeration until the $O.D._{600}$ was about 0.6. The culture was collected by centrifugation at 4000Xg for 10 minutes at 4° C., resuspended in 100 ml of cold 50 mM $CaCl_2$, and incubated on ice for 15 to 30 minutes.

The cells were again collected by centrifugation and resuspended in 10 ml of cold 50 mM $CaCl_2$ containing 20% glycerol. A 200 μl aliquot of the cells was added to the ligated DNA prepared above. The cell-DNA mixture was incubated on ice for one hour, centrifuged, and the cell pellet was resuspended into 0.5 ml of L broth in a 1.5 ml tube and incubated with aeration at 37° C. for one-half hour.

Aliquots of the transformation mixture were plated on L-agar plates containing 200 μg apramycin/ml, 40 μg X-gal/ml, and 40 μg IPTG/ml. IPTG serves to derepress the lac promoter present on plasmid pOJ160. The plates were incubated at 37° C. overnight. Colonies that contain a plasmid without an insert, such as *E. coli* K12 RR1ΔM15/pOJ160, appear blue on these plates. Colonies that contain a plasmid with an insert, such as *E. coli* K12 RR1ΔM15/pOJ313, are white. Several apramycin-resistant, white colonies were selected and then screened by restriction enzyme analysis of their plasmid DNA. Unwanted vectors were differentiated from plasmids pOJ313 and pOJ313A by digestion with restriction enzymes such as AhaIII and XbaI. These sites are present in portions of plasmid pOJ171 derived from plasmid pKC462A but are completely absent in the *Streptomyces thermotolerans* DNA insert portion of pOJ171, which contains the carE gene. Plasmid DNA was obtained from the *E. coli* K12 RR1ΔM15/pOJ313 transformants in accordance with the procedure for isolating plasmid pOJ160 DNA, described above. The plasmid pOJ313 DNA can be used to transform Streptomyces, as described in Examples 5 and 6, below.

EXAMPLE 4

Construction of Plasmids pOJ230 and pOJ231

The polylinker in the lacZα-fragment-encoding DNA of plasmid pOJ160 contains a BamHI restriction enzyme cleavage site. Plasmid pOJ160 was digested with restriction enzyme BamHI, treated with alkaline phosphatase, and ligated with the ~2.4 kb, carE-containing, BamHI restriction fragment of plasmid pOJ159. This ligation produced plasmids pOJ230 (FIG. 5) and pOJ231. The ligated DNA was used to transform *E. coli* and transformants analyzed as described in Example 3.

EXAMPLE 5

Transformation of *Streptomyces ambofaciens* With Vectors Containing the carE Gene

A. List of Solutions

The following solutions are referred to throughout the Examples and are presented here for clarity.

| Ingredient | Amount | |
|---|---|---|
| 1. P Media (~100 ml): | | |
| Sucrose | 10.3 | g |
| $K_2SO_4$ | 0.025 | g |
| Trace element solution (see #3) | 0.2 | ml |
| $MgCl_2.6H_2O$ | 0.203 | g |
| Water | 80 | ml |
| After autoclaving add: | | |
| $KH_2PO_4$ (0.5%) | 1 | ml |
| $CaCl_2.2H_2O$ (3.68%) | 10 | ml |
| (N-tris-(hydroxymethyl)-methyl-2-aminoethane sulphonic acid), "TES" buffer, 0.25 M, pH = 7.2 | 10 | ml |
| 2. Trace element solution (~1 L): | | |
| $ZnCl_2$ | 40 | mg |
| $FeCl_3.6H_2O$ | 200 | mg |
| $CuCl_2.2H_2O$ | 10 | mg |
| $MnCl_2.4H_2O$ | 10 | mg |
| $Na_2B_4O_7.10H_2O$ | 10 | mg |
| $(NH_4)_6Mo_7O_{24}.4H_2O$ | 10 | mg |
| $H_2O$ | 1 | L |
| 3. R2 Regeneration Media (~1 L): | | |
| Sucrose | 103 | g |
| $K_2SO_4$ | 0.25 | g |
| Trace element solution | 2 | ml |
| $MgCl_2.6H_2O$ | 10.12 | g |
| glucose | 10 | g |
| L-asparagine.1$H_2O$ | 2.0 | g |
| casamino acids | 0.1 | g |
| Agar | 22 | g |
| Water | to 700 | ml |
| *Yeast extract | 5 | g |
| The pH is adjusted to pH = 7.2 before autoclaving. | | |
| After autoclaving, add: | | |
| $KH_2PO_4$ (0.05 g/100 ml) | 100 | ml |
| $CaCl_2$ (2.22 g/100 ml) | 100 | ml |
| TES Buffer (5.73 g/100 ml, pH = 7.2) | 100 | ml |
| 4. Soft Nutrient Agar (SNA, ~1 L): | | |
| Difco Bacto Nutrient Broth | 8 | g |
| Agar | 5 | g |
| 5. R2YE medium is R2 medium with 20 ml of 25% yeast extract added per liter. | | |
| 6. Yeast Extract-Malt Extract (YEME, ~1 L): | | |
| Yeast extract | 3 | g |
| Peptone | 5 | g |
| Malt extract | 3 | g |
| Glucose | 10 | g |
| 7. YEME + 34% Sucrose Liquid Complete Media is YEME with 340 g/L of sucrose. | | |
| 8. YMX Media (~1 L): | | |
| Yeast extract | 3 | g |
| Malt extract | 3 | g |
| Glucose | 2 | g |
| Agar | 20 | g |
| 9. YMX Agar is 0.3% yeast extract, 0.3% malt extract, 0.2% dextrose, and 2.0% agar. | | |
| 10. CSI Media (~1 L): | | |
| Soybean meal | 15 | g |
| Casein | 1 | g |
| Cerelose | 25 | g |
| Blackstrap molasses | 3 | g |
| $CaCO_3$ | 2.5 | g |
| Czapek Mineral Stock | 2 | ml |
| Water (deionized) | 1 | L |
| pH adjusted to 7.2 prior to sterilization | | |
| 11. Czapek's Mineral Mix (~1 L): | | |
| KCl | 100 | g |
| $MgSO_4.7H_2O$ | 100 | g |
| Deionized Water | 900 | ml |
| $FeSO_4.7H_2O$ (2 g) was dissolved in 100 ml deionized water containing 2 ml of concentrated HCl. This solution was added to the above KCl/$MgSO_4.7H_2O$ solution to complete preparation of the Czapek's Mineral Mix. | | |
| 12. Bennett's Agar (~1 L): | | |

-continued

| Ingredient | Amount |
| --- | --- |
| Deionized H$_2$O | 1000 ml |
| Potato Dextrin | 10 g |
| N-Z Amine A | 2 g |
| Gibco bactoagar | 15 g |
| Gibco beef extract | 2 g |
| Yeast extract | 1 g |
| Czapek's mineral stock | 2 ml |
| 13. AS1 (~1 L) | |
| Yeast Extract | 1 g |
| L-alanine | 0.2 g |
| L-arginine (free base) | 0.2 g |
| L-asparagine | 0.5 g |
| Soluble starch | 5 g |
| NaCl | 2.5 g |
| Na$_2$SO$_4$ | 10 g |
| Meer Agar | 20 g |
| H$_2$O | to 1 L |
| Adjust pH to 7.5 with NaOH | |

*For use in *Streptomyces ambofaciens* transformations only.

B. Preparation of *Streptomyces ambofaciens* Protoplasts Transformation, and Culture Plasmids pOJ159, pOJ171, pOJ230, pOJ231, and pOJ313 were individually used to transform *Streptomyces ambofaciens* in substantial accordance with the procedure set forth below.

*Streptomyces ambofaciens* was plated on Bennett's agar and incubated at 30° C. for about 72 hours. A spore scraping was removed from the plate and used to inoculate 10 ml of TSB. The culture was incubated in an air-shaker incubator at 30° C. for ~30 hours. This culture was homogenized; then, 3 ml of the culture were used to inoculate 17 ml of TSB containing 0.4% glycine. The culture was incubated in an air-shaker incubator at 30° C. for about ~24 hours. This culture was again homogenized; then, 3 ml of the culture were used to inoculate 17 ml of TSB containing 0.4% glycine. The culture was incubated at 30° C. for about 16 hours. The culture was again homogenized; then, the mycelial fragments were harvested and washed with a 10.3% sucrose solution. The mycelial fragments were resuspended in 20 ml of P media containing 1 mg/ml lysozyme, and the resulting solution was incubated at room temperature for about one to one-and-one-half hours. During this protoplasting step, the cells were pipetted up and down to disperse clumps. The protoplasts were collected and washed two times with P medium. The protoplasts were then suspended in 10 ml of P medium. This process usually generates about 2 to 5×10$^7$ protoplasts per 200 μl of solution.

Approximately 150 μl of the protoplast solution were used per transformation. About 1 μg of the transforming DNA, in 10 μl of either ligation or TE buffer, was added to the protoplasts; then, about 100 μl of 50% polyethylene glycol 1000 (Sigma) in P media were added to and mixed with the protoplasts. The cell-DNA mixture was vortexed and then plated onto R2 medium (Example 3A3); each plate was inoculated with about 0.1 ml of cells mixed with ~3 ml of R2-modified soft agar (103 g sucrose, 0.5% agar 10.12 g MgCl$_2$, 2.22 g CaCl$_2$, and 5.72 g TES at pH =7.2 per liter). The plates were incubated at 30° C. overnight (~16 hours) and then overlaid with ~3 ml of R2-modified soft agar containing enough apramycin or thiostrepton to give a final concentration, after diffusion, of 25 μg/ml. The plates were then incubated for about four days at 30° C., when colonies became visible to the unaided eye.

C. Plate-Plug Assay

*Streptomyces ambofaciens* transformants containing plasmids pOJ159, pOJ171, pOJ230, pOJ231, or pOJ313 were patched from the R2-agar regeneration plates to plates containing AS1 and 25 μg/ml apramycin and incubated at 30° for 2–3 days until the colonies were ~5 millimeters in diameter. The colonies were then plugged and the plugs transferred, using a sterile transfer tube (Spectrum Medical Industrial, Inc., Los Angeles, Calif. 90054) to trypticase soy agar (TSA) plates, which had been previously overlayed with soft-agar nutrient broth (Difco Laboratories, Detroit, Mich. 48232) containing *Micrococcus luteus* X160 (ATCC 9341). The plates were incubated at 37° C. for 16–24 hours. *Micrococcus luteus* (ATCC 9341) is sensitive to spiramycin and isovaleryl spiramycin and resistant to apramycin. Consequently, this *M. luteus* strain cannot grow around a plug which contains Streptomyces that are producing spiramycin or isovaleryl spiramycin.

*Streptomyces ambofaciens* transformants were patched onto AS1 containing 25 μl of apramycin and 0.5 mg/ml of L-leucine (the substrate for acylase). A plug assay was performed to determine whether the colonies had begun to produce spiramycin. After two to three more days, plugs were removed for bioautography, described in part D of this example.

The plate-plug assay was used to indicate production of antibiotic by *Streptomyces ambofaciens*, which normally produces spiramycin in AS1 medium. The production of spiramycin results in zones of inhibition of *Micrococcus luteus* growth around the plug. Several additional days of incubation at 30° C. were required for conversion of the endogenously-produced spiramycin to isovaleryl spiramycin in the cultures harboring a carE expression vector. *S. ambofaciens* transformed with plasmid pOJ159 were maintained on R2 and AS1 media containing 25 μg/ml of thiostrepton, but because *M. luteus* is sensitive to thiostrepton, antibiotic production could not be measured as above. *S. ambofaciens/*pOJ159 cultures were incubated about six days before plugs were used for bioautography. Thiostrepton was included as a standard on chromatography plates when *S. ambofaciens*/pOJ159 and *S. lividans* TK23/pOJ159 cultures were assayed by bioautography.

D. Bioautography

Several plugs were prepared from the plates containing the *Streptomyces ambofaciens* and *S. lividans* transformants of the invention. These plugs were placed onto a thin-layer chromatography plate (Merck, P.O. Box 2000, Rahway, N.J. 07065, pre-coated silica gel #60 F-254) next to samples of spiramycin and isovaleryl spiramycin standards. The plugs were left on the plate for a time sufficient for diffusion to occur; then, the plate was subjected to ascending liquid chromatography in 95:5:5 ethylacetate:diethylamine:methanol. The developed chromatograms were dried thoroughly in a fume hood for at least two hours. The chromatograms were then placed face down on *Micrococcus luteus* X160-seeded TSA plates for ~15 minutes. The chromatograms were removed from the plates, and the plates were incubated at 37° for 16–24 hours.

The chromatograms for the plugs prepared from the *Streptomyces ambofaciens* transformants produced zones of inhibition resulting from substances on the chromatogram that comigrated with the isovaleryl spiramycin standard.

EXAMPLE 6

Transformation and Culture of *Streptomyces lividans*

A. Preparation of *Streptomyces lividans* Protoplasts, Transformation, and Culture

*Streptomyces lividans* TK23 (NRRL 15826) was plated on R2 agar, and the plates were incubated at 30° C. for 16 hours. A plug of cells was taken from the plate and used to inoculate 10 ml of TSS-glycine (12% sucrose and 0.5% glycine in TSB). This culture was incubated at 30° C. for ~65 hours with aeration. The culture was then homogenized, sonicated, pelleted with centrifugation, and washed with 10 ml of P media. The cell pellet was resuspended in P media containing 2 mg/ml lysozyme, incubated at 4° C. for 15 minutes, mixed by inversion, and then incubated at 4° C. for 30 minutes. The resulting protoplasts were washed twice in P media and then resuspended in 10 ml of P media. For each sample of transforming DNA (~5 μg), 200 μl of protoplasts were added to the DNA, and then, 0.5 ml of 20% polyethylene glycol 1000 in P media was added to the cell-DNA mixture. The cells were then plated in 200 μl aliquots using ~3 ml of R2-modified overlays (103 g sucrose, 10.12 g MgCl$_2$, 2.22 g CaCl$_2$, and 5.73 g TES at pH=7.2 per liter). The plates were incubated at 30° C.

The plates were incubated at 30° C. overnight (~16 hours) and then overlaid with ~3 ml of R2-modified agar (103 g sucrose, 10.12 g MgCl$_2$, 2.22 g CaCl$_2$, and 5.72 g TES at pH=7.2 per liter) containing enough thiostrepton or apramycin to give a final concentration, after diffusion, of 25 μg/ml. The plates were then incubated for about four days at 30° C., when colonies became visible to the naked eye.

The transformants were patched onto AS1 media supplemented with apramycin or thiostrepton (25 μg/ml), 0.5 μg/ml leucine, and 100 μg/ml of spiramycin and allowed to grow several days, until sporulation and pigmentation indicated well-established growth. Plugs were then removed for bioautography, performed as described in the previous Example.

EXAMPLE 7

Construction of Plasmid pOJ235

The coding sequence of the carE gene can be reconstructed by first isolating the 5' end of the coding sequence from plasmid pOJ231 (or plasmid pOJ230) on an ~700 bp PstI-BamHI restriction fragment. This fragment is purified and then digested with restriction enzyme SfaNI. The ~100 bp SfaNI-PstI restriction that results from this digestion is then isolated, purified, and ligated with NdeI-PstI-digested plasmid pUC19 and the following linker:

The ligation produces plasmid pOJ232, which then serves as a source for an ~130 bp NdeI-PstI restriction fragment that encodes the 5' end of the coding sequence of the carE gene.

The remainder of the carE coding sequence can be obtained on an ~1.7 kb BamHI-PstI restriction fragment of plasmid pOJ231 (or plasmid pOJ230). This ~1.7 kb BamHI-PstI restriction fragment of plasmid pOJ231 is ligated with the ~130 bp NdeI-PstI restriction fragment of plasmid pOJ232 and the ~5.8 kb NdeI-BamHI restriction fragment of plasmid pCZR336 to yield plasmid pOJ235. Plasmid pOJ235 drives expression of the carE gene product at temperatures above ~37° C. (at which temperature the cI857 λpL repressor is inactivated) in *E. coli*.

The ~5.8 kb NdeI-BamHI fragment from pCZR336 contains DNA sequences coding for the λpL promoter, a translation activating sequence, the cI857 repressor, a plasmid origin of replication, and a tetracycline resistance-conferring gene. Plasmid pCZR336 also contains a coding sequence for human growth hormone. The DNA sequences contained in the ~5.8 kb NdeI-BamHI fragment of plasmid pCZR336 can be constructed as described below.

Figure 7:
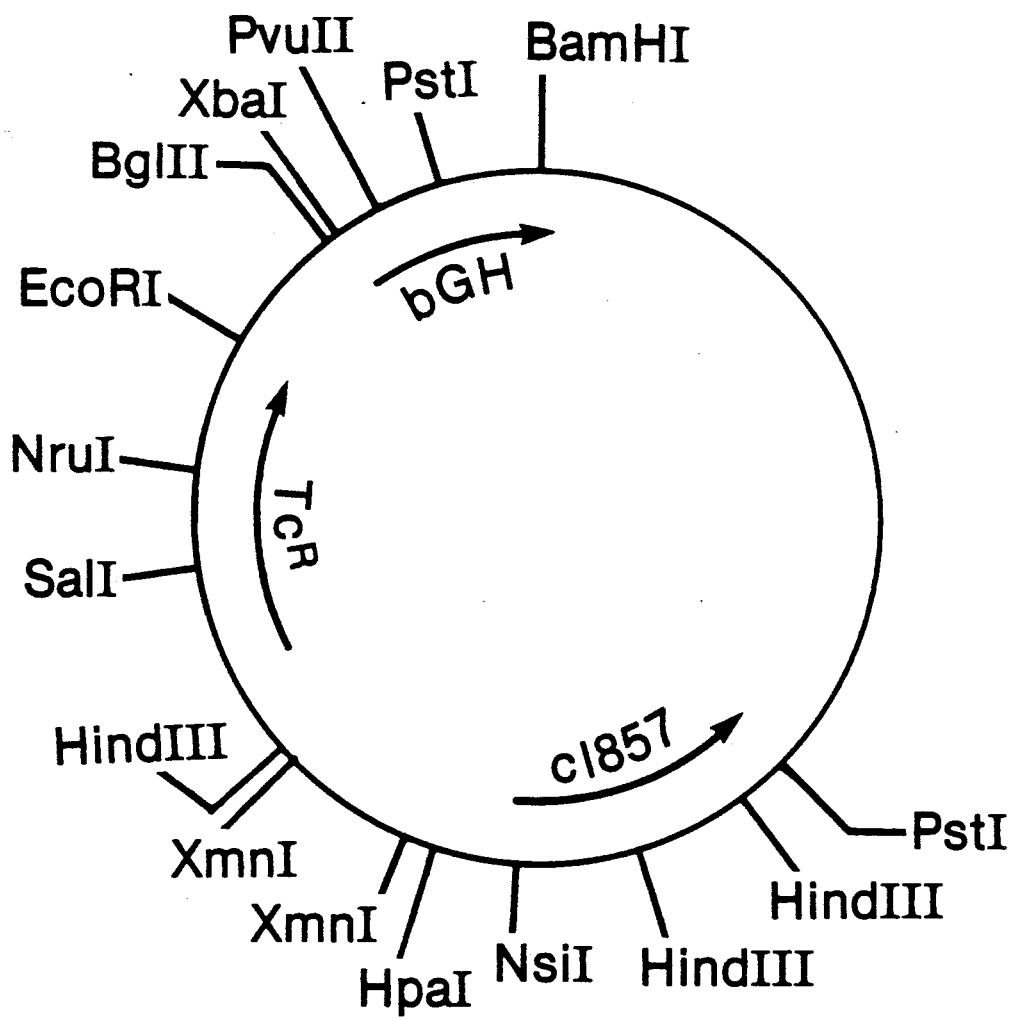
FIG. 7 is a restriction site and function map of plasmid pCZR111.

Most of the DNA in the ~5.8 kb NdeI-BamHI restriction fragment of plasmid pCZR336 can be isolated from plasmid pCZR111 on an ~5.75 kb XbaI-BamHI restriction fragment. A restriction site and function map of plasmid pCZR111 is presented in FIG. 7 of the accompanying drawings. Plasmid pCZR111 can be obtained from *E. coli* K12 RV308/pCZR111, available from the NRRL under accession number NRRL B-18249. Plasmid pCZR111 confers resistance to 10 μg/ml tetracycline and lacks a ClaI restriction site.

Plasmid pCZR111 is digested with XbaI and BamHI enzymes, and the large XbaI-BamHI fragment is purified from agarose. This XbaI-BamHI restriction fragment of plasmid pCZR111 is ligated together with a double stranded DNA fragment to yield the ~5.8 kb NdeI-BamHI restriction fragment of plasmid pCZR336. The double stranded DNA fragment has the following sequence:

Those skilled in the art recognize that the fewer DNA fragments required for a ligation, the greater the likelihood that the desired plasmid will be produced by the ligation. Thus, plasmid pOJ235 could be constructed by using the 5.75 kb XbaI-BamHI fragment of plasmid pCZR111 and the DNA fragment described above in place of the single ~5.8 kb NdeI-BamHI fragment in the construction protocol for plasmid pOJ235, but yields of the desired plasmid would probably be lower. Plasmid pOJ235 drives expression of the carE gene product in *E. coli*.

We claim:

1. A method for increasing the amount of 4"-O-isovalerylacylase enzyme in an organism that comprises (1) transforming said organism with a recombinant DNA vector that codes for expression of the Streptomyces carE gene product; and (2) culturing said organism transformed in step (1) under conditions that allow for gene expression.

2. The method of claim 1, wherein said organism is Streptomyces.

3. The method of claim 1, wherein said organism is *Streptomyces ambofaciens*.

4. The method of claim 1, wherein said organism is *Streptomyces lividans*.

5. The method of claim 1, wherein said organism is *Streptomyces thermotolerans*.

6. The method of claim 1, wherein said organism is *Streptomyces fradiae*.

7. A constructed DNA compound that encodes a Streptomyces 4"-Oisovaleryl acylase enzyme.

8. The constructed DNA compound of claim 7 that encodes the 4"-O-isovaleryl acylase enzyme of *Streptomyces thermotolerans*.

9. The constructed DNA compound of claim 8 that encodes an acylase with the amino acid residue sequence:

H₂N-Met Pro Leu Pro Lys His Leu Pro Ala Leu Gly Gly
Met Arg Phe Ile Ser Ala Leu Leu Val Phe Thr Ser His
Ile Ser Thr Gln Pro Phe Lys Asn Thr Glu Ile Asn
Ser Ala Leu Gln Phe Pro Leu Asn Arg Leu Gly Pro Leu
Thr Val Ser Phe Phe Phe Met Leu Ser Gly Phe Val Leu
Thr Trp Ala Gly Leu Pro Asp Lys Ser Lys Val Asn Phe
Trp Aeg Aeg Arg Thr Val Arg Ala Tyr Ser Leu His Leu
Pro Val Leu Leu Val Thr Leu Leu Ile Val Leu Ala Leu
Asn Glu Pro Asn Met Gly Arg Ser Val Trp Asp Gly Leu
Leu Thr Asn Leu Leu Leu Ile Gln Ala Trp Phe Pro Asp
His His Glu Tyr Gly Ser Met Asn Pro Val Ala Trp Ser
Leu Ser Cys Glu Leu Phe Phe Tyr Ala Met Phe Pro Phe
Leu Phe Ala Phe Phe Thr Lys Val Arg Thr Asp Arg Leu
Trp Arg Trp Ala Ala Ala Val Ser Val Ala Ala Val Ser
Ile Pro Leu Val Ala Leu Leu Leu Pro Ala Ser Pro Pro
Leu Pro Trp Asp Pro Asp Met Pro Gln Leu Arg Trp Trp
Phe Ile Tyr Met Phe Pro Pro Val Arg Leu Leu Glu Phe
Val Leu Gly Met Leu Met Ala Gln Ile Val Ile Arg Gly
Arg Trp Arg Gly Pro Arg Pro Leu Ala Cys Val Ala Leu
Phe Ser Ala Val Phe Ala Val Thr Phe Ala Val Pro Asn
His Tyr Asp Pro Gly Ala Leu Thr Val Pro Val Ile Ala
Leu Leu Leu Ala Ser Val Ala Val Gly Asp Val Arg Gly
Val Arg Ser Trp Leu Gly Thr Arg Thr Met Val Leu Leu
Gly Glu Leu Thr Phe Ala Phe Tyr Leu Val His Tyr Leu
Ile Ile Gln Tyr Gly His Arg Phe Ala Gly Gly Lys Gln
Gly Tyr Tyr Arg Gln Trp Asp Thr Pro Ala Ala Val Gly
Leu Thr Leu Leu Ala Phe Thr Leu Ala Leu Gly Leu Ser
Ala Phe Leu His Phe Phe Val Glu Lys Pro Val Met Arg
Thr Leu Gly Arg Pro Arg Arg Ser Pro Asp Ala Gly Ser
Thr Pro Arg Ser Glu Pro Ala Ser Gly Thr Pro-COOH, wherein Ala is an alanine, Arg is an arginine, Asn is an asparagine, Asp is an aspartic acid, —COOH is the carboxy terminus, Cys is a cysteine, Gln is a glutamine, Glu is a glutamic acid, Gly is a glycine, H₂N— is the amino terminus, His is a histidine, Ile is an isoleucine, Leu is a leucine, Lys is a lysine, Met is a methionine, Phe is a phenylalanine, Pro is a proline, Ser is a serine, Thr is a threonine, Trp is a tryptophan, Tyr is a tyrosine, and Val is a valine.

10. The DNA constructed compound of claim 9 that is

5'-ATG CCC CTG CCG AAA CAT CTT CCC GCG CTC
GGC GGG ATG CGT TTC ATC TCC GCT CTA CTG
GTA TTC ACC TCC CAT ATA TCG ACA CAG CCG
TTC TTC AAG AAC ACC GAG ATC AAT TCC GCG
CTG CAG TTC CCG CTG AAC CGG CTG GGC CCG
CTG ACG GTC TCG TTC TTC TTC ATG CTC AGC
CGT TTC GTC CTC ACC TGG GCG GGT CTG CCC
GAC AAG TCC AAG GTG AAC TTC TGG CGG CGG
CGC ACG GTC CGC GCG TAC TCG CTG CAC CTG
CCC GTG CTG CTG GTG ACG CTG CTG ATC GTG
CTG GCC CTC AAC GAG CCC AAC ATG GGC CGA
TCG GTG TGG GAC GGA CTG CTC ACG AAC CTG
CTG CTG ATC CAG GCA TGG TTC CCC GAC CAC
CAC GAG TAC GGC AGC ATG AAC CCG GTG GCG
TGG TCG CTC TCC TGC GAG CTG TTC TTC TAC
GCC ATG TTC CCG TTC CTC TTC GCC TTC TTC
ACC AAG GTC CGT ACG GAC CGG CTC TGG CGG
TGG GCC GCC GCG GTG TCC GTG GCC GCC GTC
TCC ATC CCC CTG GTC GCA CTG CTG CTG CCG
GCC AGC CCG CCC CTG CCG TGG GAC CCG GAC
ATG CCG CAG CTG CGG TGG TGG TTC ATC TAC
ATG TTC CCG CCG GTG CGG CTG CTG GAG TTC
GTG CTC GGG ATG CTC ATG GCC CAG ATC GTG
ATC CGG GGA CGC TGG AGG GGC CCG CGT CCC
CTG GCC TGC GTC GCG CTG TTC TCA GCG GTG
TTC GCG GTG ACG TTC GCG CCG AAC CAC
TAC GAC CCC GGC GCG TTG ACC GTC CCG GTG
ATC GCG CTG CTG CTC GCC TCG GTG GCC GTC
GGT GAT GTG CGC GGC GTC CGC TCC TGG CTG
GGG ACC AGG ACG ATG GTG CTG CTG GGG GAA
CTC ACC TTC GCC TTC TAC CTC GTG CAC TAC
CTG ATC ATC CAG TAC GGG CAC CGC TTC GCC
GGC GGG AGG CAG GGC TAT TAC CGG CAG TGG
GAC ACA CCG GCC GCC GTC GGG CTG ACC CTG
CTC GCC TTC ACG CTG GCG CTG GGG CTG TCG
GCG TTC CTG CAC TTC TTC GTG GAG AAG CCG
GTC ATG CGA ACC CTG GGA CGG CCG CGG CGG
TCC CCG GAC GCC GGC TCG ACA CCC AGG TCC
GAA CCC GCC CCG TCC GGC ACT CCG-3' wherein A is deoxyadenyl, G is deoxyguanyl, C is deoxycytidyl, T is thymidyl.

11. A recombinant DNA vector that encodes a DNA compound of claim 9.

12. The recombinant DNA vector of claim 11 that is pOJ313.

13. The recombinant DNA vector of claim 11 that is pOJ313A.

14. The recombinant DNA vector of claim 11 that is pOJ230.

15. The recombinant DNA vector of claim 11 that is pOJ231.

16. The recombinant DNA vector of claim 11 that is pOJ235.

17. A host cell transformed with a recombinant DNA vector of claim 10.

18. The host cell of claim 17 that is Streptomyces.

19. The host cell of claim 17 that is *Streptomyces ambofaciens*.

20. The host cell of claim 17 that is *Streptomyces lividans*.

21. The host cell of claim 17 that is *Streptomyces thermotolerans*.

22. The host cell of claim 17 that is *Streptomyces fradiae*.

23. The host cell of claim 19 that is *Streptomyces ambofaciens*/pOJ230.

24. The host cell of claim 19 that is *Streptomyces ambofaciens*/pOJ313.

25. The host cell of claim 20 that is *Streptomyces lividans*/pOJ313.

26. The host cell of claim 17 that is *E. coli*.

27. The host cell of claim 26 that is *E. coli*/pOJ235.

UNITED STATES PATENT AND TRADEMARK OFFICE
CERTIFICATE OF CORRECTION

PATENT NO. : 5,068,189

DATED : November 26, 1991

INVENTOR(S) : Janet K. Epp and Brigitte E. Schoner

It is certified that error appears in the above-identified patent and that said Letters Patent is hereby corrected as shown below:

<u>COL. 23</u>

In Claim 7, line 6, please change "4"-Oisovaleryl" to -- 4"-O-isovaleryl --.

In Claim 9, line 20, please change "Aeg Aeg" to -- Arg Arg --.

In Claim 10, line 50, please change "DNA constructed" to -- constructed DNA --.

In Claim 10, line 59, please change "CGT" to -- GGT --.

Signed and Sealed this

Twenty-first Day of September, 1993

Attest:

Attesting Officer

BRUCE LEHMAN

Commissioner of Patents and Trademarks